United States Patent [19]

McMinn

[11] 4,319,565
[45] Mar. 16, 1982

[54] DEVICE FOR INCLUSION IN AN IMMOBILIZING STRUCTURE FOR A LIMB AND LIMB IMMOBILIZING STRUCTURES INCLUDING SUCH DEVICES

[76] Inventor: Derek J. W. McMinn, 14 Avon Dr., Moseley, Birmingham 13, England

[21] Appl. No.: 142,413

[22] Filed: Apr. 21, 1980

[30] Foreign Application Priority Data

Apr. 24, 1979 [GB] United Kingdom ............... 14252/79

[51] Int. Cl.³ .............................................. A61F 5/04
[52] U.S. Cl. ................................ 128/87 R; 128/91 R; 128/119
[58] Field of Search .............. 128/87, 87 A, 90, 92 R, 128/91, 92 A, 82, 83, 119

[56] References Cited

U.S. PATENT DOCUMENTS

| 33,980 | 12/1861 | Bryan | 128/119 |
|---|---|---|---|
| 1,221,016 | 4/1917 | Best | 128/119 |
| 2,904,040 | 9/1959 | Hale | 128/87 R |
| 3,116,731 | 1/1964 | Baxter | 128/91 R |
| 3,439,673 | 4/1969 | Sprecher | 128/87 R X |

FOREIGN PATENT DOCUMENTS 2324456 11/1974 Fed. Rep. of Germany .... 128/91 R

*Primary Examiner*—Stephen C. Pellegrino
*Attorney, Agent, or Firm*—Trexler, Bushnell & Wolters, Ltd.

[57] ABSTRACT

A splint for a fracture includes a spring-loaded device for applying a pressure to prevent relative movement between parts of a fractured bone in a limb within the splint. The device accommodates and takes up swelling of surrounding tissue, as well as volume changes due to flexing of surrounding muscles. The device is re-usable after the splint is removed.

7 Claims, 3 Drawing Figures

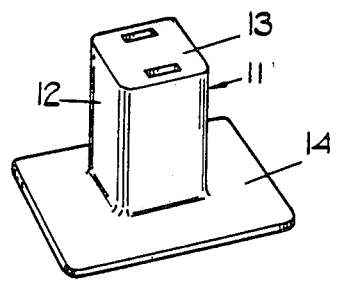
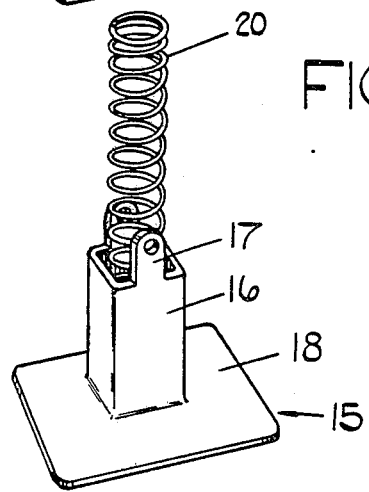
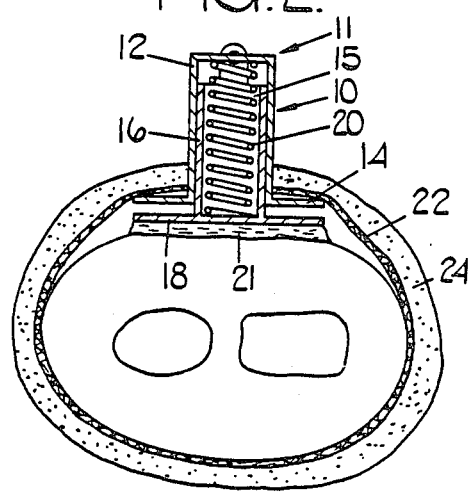
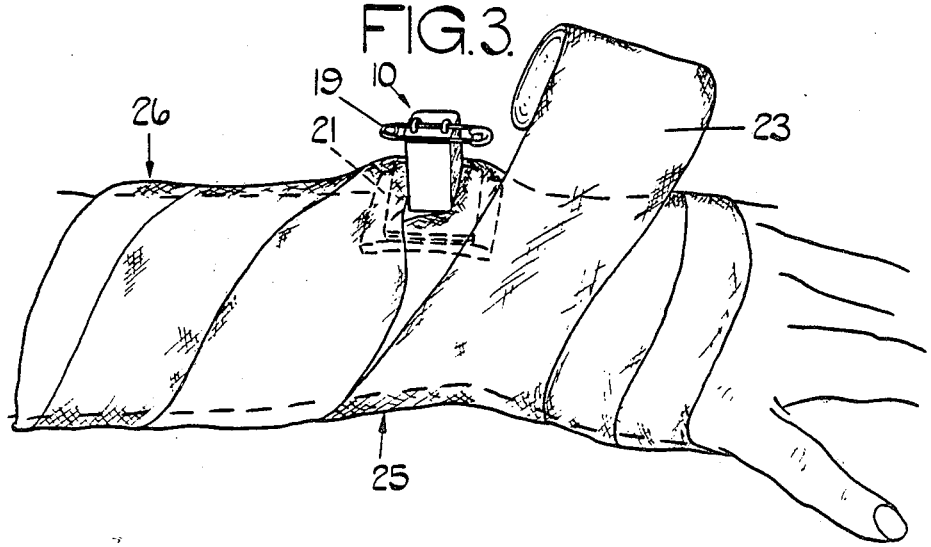

DEVICE FOR INCLUSION IN AN IMMOBILIZING STRUCTURE FOR A LIMB AND LIMB IMMOBILIZING STRUCTURES INCLUDING SUCH DEVICES

This invention relates to a device for inclusion in a splint structure for a limb and also to a splint structure incorporating such a device.

It is common medical practice to use a splint structure, for example, a plaster cast, for immobilising a limb or a part thereof, and in particular to apply a splint structure to a limb having a bone fracture, after the fracture has been reduced. Fractures are usually accompanied by swelling of the surrounding tissues, the swelling decreasing after the fracture is reduced. After the swelling have decreased the splint structure will no longer be firm at the area of the fracture. Additionally, muscle movement causes redistribution of the volume of the limb tissues within the splint, and the relative positions of the fractured bone parts may thereby be altered during the healing process. Such alteration can adversely affect the subsequent mobility of the limb.

It is an object of the invention to provide a device for incorporation in a splint structure to improve the effect of the structure in restraining relative movement between the parts of a bone on opposite sides of a fracture.

It is a further object of the invention to provide a splint structure having an improved effectiveness in restraining the aforesaid relative movement.

According to the invention there is provided a device for incorporation in an immobilising structure for a limb, said device comprising a first part adapted to be secured to said structure, a second part for engaging a limb which is immobilised by said structure, and a spring engaged between said first and second parts, for biasing said second part into engagement with said limb.

According to a further aspect of the invention there is provided a limb-immobilising structure incorporating a device as aforesaid.

An embodiment of the invention will now be described by way of example only, and in relation to a device and structure as applied to a Colles's fracture of the radial bone. In the drawings:

FIG. 1 is an exploded view of a device according to the invention,

FIG. 2 is a section through a human forearm surrounded by a plaster splint structure which includes the device of FIG. 1, and FIG. 3 shows a stage in the application of the splint of FIG. 2.

As shown, the device 10 has a first part 11 comprising a square tube 12 having a closure element 13 at one end and a rectangular plate 14 at the other end. A second part 15 comprises a square tube 16 which can be slidably received by the tube 12 and which has at one end two lugs 17 which can pass through rectangular holes in the closure element 17. A rectangular plate 18 is secured across the other end of the tube 16, corresponding sides of the plates 14, 18 having equal lengths. The lengths of the tubes 12, 16 are such that when the tube 16 is within the tube 12 and the plates 14, 18 are in contact, a retaining pin 19 (FIG. 3) may be inserted through the holes in the lugs 17 to retain the parts 11, 15 in this relative position. A compression spring 20 is located between the plate 18 and the element 13 to bias the parts 11, 15 apart. Preferably, the plate 18 has an area of not less than 4 square centimeters. The plate 18 may, however, have edges which are up to 5 and 4 centimeters in length, thereby having a total effective area of 20 square centimeters.

FIGS. 2 and 3 show the device 10 included in a plaster splint for a Colles's fracture of the radius. The fracture is first reduced manually and held in this condition. As shown in FIGS. 2 and 3 a felt pad 21 is interposed between the patient's wrist and the plate 18, the plate 18 having its longer median line located over the ulnar styloid. The part 15 is secured in this position by suitable adhesive tape. The spring 20 and part 11 are then assembled onto the part 15 and held with the spring 20 compressed, by means of the pin 19, as shown in FIG. 3. Suitable padding 22 is placed around the limb and a splint is applied, by means of a plaster bandage 23, holding the part 11 in position. The plaster splint 24 is applied so as to have a concavity at a location 25, and thereby to apply a pressure to the volar aspect of the distal radius proximal to the fracture. The plaster splint is also formed so as to exert a pressure at a zone 26. Since the device 10 exerts pressure over the back of the radius distal to the fracture line, a three-point fixing of the relative parts of the fractured bone is achieved. This fixing is maintained by the action of the device 10, even though tissue swelling reduces, and also during movement of the muscles of the forearm.

It will be apparent that generally similar procedures, modified as appropriate, may be used for different types of fracture and different locations. It will also be apparent that the plate 18 may be other than flat, if such a configuration is required for a particular type of fracture.

Preferably, the parts 11, 15 are of plastics material and may therefore be easily fabricated, as well as permitting the passage of X-rays. After the plaster has been removed from the patient, the device 10 may readily be pressed out of the plaster and is then available for reuse.

Tests have indicated that a device and splint structure according to the invention will effect a substantial reduction in the percentage of Colles's fractures which slip during the period of splint application.

I claim:

1. A device for incorporation in a splint for a limb, said device comprising a rigid first part which includes locating means for engaging a recess in said splint so as to prevent rotation of said first part within the recess, said first part also including means for restraining linear movement of the first part away from a limb within the splint, a rigid second part for engaging a limb within the splint, said second part being slidably engageable with said first part, means for preventing relative rotation between said parts, and a spring engageable with said parts for biasing said second part into contact with a limb within said splint.

2. A device for incorporation in a splint for a limb, said device comprising a first part which includes a rigid tubular portion of non-circular cross-section which is engageable in a recess in said splint, a flange on said tubular portion engageable with an inner surface of said splint to restrain said first part against movement away from a limb within the splint, a rigid second part for engaging a limb within the splint, said second part being slidably engageable with said first part, means for preventing relative rotation between said parts, and a spring engageable with said parts for biasing said second part into engagement with said limb.

3. In combination with a splint for a limb, a device for applying a local pressure to a portion of the limb, said device comprising a rigid first part which includes means for engaging a recess in the splint so as to prevent rotation of said first part within the recess, said first part also including means for preventing movement thereof outwardly of said splint and away from the limb, a rigid second part slidably engaging said first part and being engageable with said limb, means for preventing relative rotation between said parts, and a spring engaged between said parts for biasing said second part into contact with the limb.

4. The combination claimed in claim 3 in which said first part comprises a tubular portion of non-circular cross-section and a flange on said tubular portion.

5. The combination claimed in claim 3 or claim 4 in which portions of said first and second parts project outwardly of said splint and there is provided means on said projecting portions for retaining said parts in a predetermined relative position in which said spring is compressed.

6. A splint assembly for immobilizing a limb, comprising a plaster splint shaped so as to apply pressure at two zones on said limb which are spaced lengthwise thereof, and a spring loaded device located in said splint at a location spaced lengthwise of the limb from each of said two zones, said device including a part biased so as to engage said limb at said location, said two zones and said location being arranged to lie alternately on opposite sides of said limb, whereby said assembly applies pressure at three predetermined points of said limb.

7. A method of applying pressure at three predetermined points of a limb within a splint, comprising forming the splint so as to apply pressure to two zones on said limb which are spaced lengthwise thereof, and incorporating into the splint a spring-loaded device, one part of which is biased into engagement with said limb at a location thereon spaced lengthwise of the limb from each of said two zones, said two zones and said location being arranged so as to lie alternately on opposite sides of the limb.

* * * * *